United States Patent [19]

Hart

[11] 4,078,050

[45] Mar. 7, 1978

[54] DEODORANT COMPOSITIONS AND PROCESS OF DEODORIZING USING 2,4-DISUBSTITUTED 6-HYDROXY-1,3-DIOXANE COMPOUNDS

[76] Inventor: Una L. Hart, 1750 Summit Ave., Saint Paul, Minn. 55105

[21] Appl. No.: 702,905

[22] Filed: Jul. 6, 1976

Related U.S. Application Data

[63] Continuation-in-part of Ser. No. 527,623, Nov. 27, 1974, abandoned, which is a continuation-in-part of Ser. No. 410,241, Oct. 29, 1973, Pat. No. 3,903,259, and a continuation-in-part of Ser. No. 104,769, Jan. 7, 1971, abandoned, which is a continuation-in-part of Ser. No. 782,474, Dec. 9, 1968, abandoned.

[51] Int. Cl.$^2$ .................. A61L 13/00; A01N 9/28
[52] U.S. Cl. .................. 424/76; 260/340.7; 424/278
[58] Field of Search .............. 424/76, 278; 260/340.7

[56] References Cited

U.S. PATENT DOCUMENTS 3,772,443  11/1973  Wessendorf et al. .................. 424/78

OTHER PUBLICATIONS

Hanschke, C.A. vol. 37 (1943), pp. 5374–5375.
Spath et al., C.A. vol. 37 (1943), pp. 4695–4696.
Murray, C.A. vol. 38 (1944), p. 1475.
Shantarovich et al., C.A. vol. 65 (1966), p. 12197.

*Primary Examiner*—Allen J. Robinson
*Attorney, Agent, or Firm*—Harold J. Kinney

[57] ABSTRACT

Offensive odors of animal origin are lessened or neutralized by application of deodorant compositions comprising 2,4-di (alkyl or aryl) substituted 6-hydroxy-1,3-dioxanes. The effectiveness of the compositions toward specific odors is increased by incorporation of acidic or basic components. The compositions can be further improved by the addition of other ingredients such as surfactants, chelating agents and antimicrobial agents.

15 Claims, No Drawings

DEODORANT COMPOSITIONS AND PROCESS OF DEODORIZING USING 2,4-DISUBSTITUTED 6-HYDROXY-1,3-DIOXANE COMPOUNDS

This application is a continuation-in-part of my copending application Ser. No. 527,623 filed Nov. 27, 1974, now abandoned, which is a continuation-in-part of Ser. No. 410,241, now Pat. No. 3,903,259, filed Oct. 29, 1973 as a continuation-in-part of Ser. No. 104,769 filed Jan. 7, 1971, abandoned, which is a continuation-in-part of Ser. No. 782,474 filed Dec. 9, 1968, abandoned.

This invention relates to the controlling or neutralizing of offensive odors of animal origin and to novel deodorant materials and compositions for use therein.

Previous methods of controlling offensive odors, including those associated with animals, involved affecting the sense of smell. One older method was the use of a strong chemical such as formaldehyde which reacts with the olfactory epithelium (sense organ) so that it is physiologically inactivated, that is, the sense of smell is temporarily destroyed. Another method, currently popular, is to overwhelm the sense of smell with a very strong odor so that the objectionable odor is no longer detected. These strong odors are usually perfumes and are commonly called masking agents. These are very persistent odors and often have a sweet odor so that the masking agent itself can be objectionable.

A feature of the present invention resides in the provision of deodorant compositions which rapidly eliminate or greatly reduce offensive odors, leaving little or no persistent odor of their own. I have found that various lower alkyl or aryl substituted 6-hydroxy-1,3-dioxanes, e.g. as hereinafter illustrated, may serve as effective deodorants, and that their deodorant action against certain odors is increased in mildly acidic and mildly basic media. With some of these compounds, any slight residual odor may be further decreased or rendered innocuous by using fractional proportions of two or more.

The deodorant compound or mixture of compounds is best applied from solution or suspension in a volatile liquid vehicle. Water is a preferred vehicle but organic solvents may be used in whole or in part where desired for greater solubility or for other reasons.

A further feature of the present invention resides in the provision of deodorant compositions of the types described which in their preferred forms contain a surfactant or wetting agent. The purposes of the surfactant are to increase the rates at which the deodorant solutions penetrate sources of odors in order to speed up the rates of deodorization and to aid in the removal of any residual materials from fabrics, rugs and floors. The amount of surfactant would normally be small, but larger amounts of surfactants could be used to prepare solutions for deodorizing pets who have encountered a skunk or rolled in dead fish or the like.

An added feature of the present invention resides in the provision of deodorants of the types described which in their preferred forms contain a chelating agent to aid in stain removal.

Another feature of the present invention resides in the provision of deodorants of the types described, which in their preferred forms contain an antimicrobial agent which will aid in the deodorization process by inhibiting the growth of microorganisms and thereby reduce the formation of odoriferous products by them. The dioxane compounds themselves are found to exhibit antimicrobial action, but other antimicrobial agents may be added for greater effectiveness.

I have discovered that unpleasant odors associated with feline animals, excreta, necrotic tissue and skunks can be greatly reduced or eliminated by treating the source of the odor with mildly acidic formulations containing one or more of the 2,4-disubstituted (alkyl or aryl)-6-hydroxy-1,3-dioxanes. Application on used cat litter eliminates the unpleasant odors which build up in cat boxes. These formulations may be also used on furniture, carpeting and flooring contaminated with excreta. For example, they have the advantage of eliminating urine odors so that the animal does not return to the same place to urinate. In veterinarians' offices, the use of these deodorants on base boards, carpeting and flooring reduces the incidence of urination by dogs. Dogs will often urinate in an area where the odor of urine is detected, but are apparently reluctant to do so if urine odor is not smelled.

In veterinary medicine and mortuary science, these deodorants are useful for deodorizing necrotic tissue.

These deodorants are also effective in greatly reducing or eliminating the odor of skunk from animals, cars, camping equipment and the like.

In the lower concentrations, these deodorant formulations are non-irritating and can be safely used on pets. The application of the deodorant solution to the genital and anal areas of tom cats effectively controls this offensive odor. Similarly, the application of the deodorant three to four times daily to the genital area of bitches in heat greatly reduces this odor so that the attraction of male dogs is greatly diminished. Application of the deodorants to pets who have rolled in dead fish or encountered a skunk controls these offensive odors also.

The alkaline deodorant formulations are effective against human perspiration odor. Laundering washable materials removes perspiration odor, but dry cleaning nonwashable materials often does not. These formulations are therefore useful to deodorize nonwashable clothing, athletic equipment and prosthetic devices which smell of perspiration.

Used on leather, the alkaline deodorant formulations have the added advantage of conditioning it. Perspiration-soaked leather hardens and becomes somewhat brittle. Application of these tyes of deodorants returns the leather to its naturally soft and pliable condition, thereby prolonging the useful life of the leather device.

The alkaline deodorant formulations are also effective in greatly reducing or eliminating dog body odor. This odor seems to emanate from facial folds, ears, and genital and anal areas of dogs. It is effectively neutralized, without harm to the animal, by the application of the mildly alkaline compositions containing the lower concentrations of the dioxane compounds.

The compound 2,4-dimethyl-6-hydroxy-1,3-dioxane has been described by Spath et al (C.A.37,4695 (1943)). Other analogous compounds have been described by Saunders et al (C.A.38, 1475 (1944)). These compounds decompose, with liberation of aldehyde, until an equilibrium is reached. Continued removal of the aldehyde then disturbs the resulting equilibrium and permits the decomposition to proceed to completion.

In accordance with methods described by Saunders et al (J.A.C.S.65, 1714-17(1943)) the deodorant compounds are readily prepared by adding 10% aqueous potassium hydroxide solution, dropwise and with vigorous agitation, to a solution of the desired aldehydes in ethyl ether maintained at suitable temperatures, ordinarily within the range of about 0°–15° C. The ether layer is separated, washed with water until no longer alkaline, and the ether evaporated to recover the crude product, which if desired may then be purified by distillation under vacuum.

These deodorant compositions may be applied in a number of ways. Perhaps the simplest is as an aerosol spray, the spray being applied directly to the odorant source material. Application from a spray bottle is also effective. In such container the dioxanes remain in stable equilibrium with their aldehydic decomposition products. In some instances the deodorant solution may simply be exposed to a current of air which is then passed into the odor-containing area, e.g. by way of a ventilating system. The deodorant composition remains in stable equilibrium when kept in a closed container, the material in plastic spray bottles being found fully effective after a two year aging period as well as when initially prepared.

The concentration of the dioxane in the deodorant composition will ordinarily range between about 0.2 and 5 percent. Acidic and basic materials, where used, may range in concentration up to about ten percent.

Suitable acidic components include organic carboxylic acids, e.g. benzoic, maleic, glycolic, pyruvic, lactic, fumaric, citric, mandelic, succinic and tartaric acids, and acidic inorganic salts, e.g. ammonium chloride and sodium dihydrogen phosphate. Suitable basic components include the inorganic basic salts, e.g. alkali metal carbonates, bicarbonates, dibasic phosphates and acetates; and non-primary organic amines such as diethanolamine and triethanolamine. These compounds control the pH of the aqueous liquid vehicle. As above indicated, for certain uses a mildly acidic formulation is preferred, and for certain other uses an alkaline formulation is preferred.

A surfactant is present in the preferred forms of the deodorants, the amount used being in the range of, for example, 0.02–5 percent. Suitable surfactants for both acidic and alkaline formulations include octyl-and/or nonylphenoxypoly(2-12)-ethyleneoxyethanol, benzene alkyl ($C_4$–$C_{15}$) sulfonate, sodium dioctylsulfosuccinate, and triethanolamine dodecylbenzenesulfonate.

A chelating agent is present in the preferred forms of the deodorants because such agents aid in stain removal. Suitable chelating agents are the disodium and tetra sodium salts of (ethylenedinitrilo) tetraacetic acid. The concentration of these compounds should ordinarily be in the range of 0.1–1 percent.

Antimicrobial agents such as sodium propionate, alkyl ($C_8$–$C_{18}$) dimethylbenzammonium chloride and 4-chloro-3-methylphenol may optionally be added, e.g. in amounts between 0.2 and 0.5 percent.

Deodorant compositions made and applied in actual use in accordance with the foregoing have been found fully effective, both as initially prepared and after prolonged storage in sealed containers, in neutralizing the offensive odors emanating from cat boxes, dog excreta, floors and carpets contaminated with cat and dog urine, and various other animal odorant sources.

Deodorant compositions prepared in accordance with a number of the following specific illustrative examples, namely, Examples 20 and 24 to 39 inclusive, all of which are acidic, have additionally been tested by controlled direct application to odorant material followed by olfactory testing after periods of minutes, hours and days. The odorant material employed consisted of five grams of odoriferous dog excreta to which two drops of deodorant composition were added, the mixture being then sealed in aluminum foil and inspected for odor after periods of 2 minutes, 1 hour, and 1 day. The same test was applied to Examples 41 and 42. In a third series, a mixture of 20 grams of used cat litter plus 2.5 grams of cat feces was treated with 5 drops of deodorant composition of Examples 30–34, sealed, and tested after periods of 2 minutes and 1 hour. In each series an untreated packet served as control. In all cases the presence of the deodorant composition was found, upon comparing the test and control packets, to greatly reduce or substantially eliminate the offensive odor.

In a further test a few drops of a synthetic odorant mixture providing a strong "doggy" odor and consisting of a number of odorous lower alkyl monocarboxylic acid (viz. a mixture of 0.1% by weight of each of glacial acetic acid, propionic acid, isobutyric acid and butyric acid and 0.2% by weight of each of isovaleric acid, valeric acid and caproic acid) were absorbed into a number of perfume test blotters and the spot on each treated with 1–2 drops of a basic deodorant composition as hereinafter illustrated, namely, Examples 15, 16, 17, 20, 23, 37, 38 and 39. The offensive odor in each test was found to be substantially completely neutralized within moments after the treatment.

It will be appreciated that some selection of components and proportions from within the ranges specified may be required in order to gain the greatest advantages or to avoid obvious difficulties, e.g. in compatibility, inter-reactivity, solubility of other factors. It will also be understood that other specific components having equivalent properties may replace all or part of many of those given in the Examples, although usually with some disadvantage. As but one example, isopropanol as a solvent or diluent may be replaced by ethanol but the latter is both more expensive and more volatile. Again, any of the dioxane compounds having excessively large substituent radicals in the 2,4 or 5 positions depolymerize too slowly and/or they (or their decomposition products) are too low in vapor pressure to accomplish deodorization at any useful rate and are therefore not preferred. Compounds such as 2-cuminyl-4-ethyl-5-methyl-6-hydroxy-1,3-dioxane (mol. wt. 278) and 2,4-diheptyl-5-hexyl-6-hydroxy-1,3-dioxane (mol. wt. 384) represent an approach to a limiting value in respect to the size of the substituent radicals. Also, low molecular weight aliphatic monoamines and diamines are strongly odoriferous, and primary amines react readily with aldehydes, so that these classes of materials are not desired in the practice of the invention. Both nonionic and anionic surfactants are effective in basic formulations, whereas the anionic materials are unstable under acidic conditions so that only the nonionic compounds are to be used under such conditions.

EXAMPLES

Examples 1. 1 g. Citric acid
   0.2 g. 2,4-dimethyl-6-Hydroxy-1,3-Dioxane
   98.8 g. Water
2. 10 g. Sodium dihydrogen phosphate
   0.5 g. 2,4-Dimethyl-6-Hydroxy-1,3-Dioxane
   89.5 g. Water
3. 2 g. Mandelic acid
   2 g. 2,4-Dimethyl-6-Hydroxy-1,3-Dioxane
   96 g. Water
4. 5 g. Ammonium chloride
   5 g. 2,4-Dimethyl-6-Hydroxy-1,3-Dioxane
   90 g. Water
5. 3 g. Succinic acid
   4 g. 2,4-Dimethyl-6-Hydroxy-1,3-Dioxane
   0.02 g. Nonylphenoxypoly (2-12) ethyleneoxyethanol

Examples-continued 6. 93 g. Water
   2 g. Tartaric acid
   3 g. 2,4-Dimethyl-6-Hydroxy-1,3-Dioxane
   2 g. Benzene alkyl ($C_4$-$C_{15}$) sulfonate
   93 g. Water
7. 2 g. Citric acid
   2 g. 2,4-Dimethyl-6-Hydroxy-1,3-Dioxane
   5 g. Nonylphenoxypoly (2–12) ethyleneoxyethanol
   91 g. Water
8. 8 g. Sodium dihydrogen phosphate
   1 g. 2,4-Dimethyl-6-Hydroxy-1,3-Dioxane
   3 g. Sodium dioctylsulfosuccinate
   88 g. Water
9. 1 g. Citric acid
   0.5 g. 2,4-Dimethyl-6-Hydroxy-1,3-Dioxane
   1 g. Triethanolamine dodecylbenzenesulfonate
   0.1 g. (Ethylenedinitrilo) tetraacetic acid, disodium salt
   97.4 g. Water
10. 3 g. Mandelic acid
    1.5 g. 2,4-Dimethyl-6-Hydroxy-1,3-Dioxane
    0.5 g. Benzene alkyl ($C_4$-$C_{15}$) sulfonate
    0.5 g. (Ethylenedinitrilo) tetraacetic acid, tetrasodium salt
    94.5 g. Water
11. 8 g. Citric acid
    2 g. 2,4-Dimethyl-6-Hydroxy-1,3-Dioxane
    0.3 g. Nonylphenoxypoly (2–12) ethyleneoxyethanol
    1 g. (Ethylenedinitrilo) tetraacetic acid, tetrasodium salt
    88.7 g. Water
12. 5 g. Succinic acid
    2.5 g. 2,4-Dimethyl-6-Hydroxy-1,3-Dioxane
    5 g. Triethanolamine dodecylbenzenesulfonate
    0.5 g. (Ethylenedinitrilo) tetraacetic acid, disodium salt
    87 g. Water
13. 6 g. Sodium dihydrogen phosphate
    1 g. 2,4-Dimethyl-6-Hydroxy-1,3-Dioxane
    0.2 g. Benzene alkyl ($C_4$-$C_{15}$) sulfonate
    0.2 g. (Ethylenedinitrilo) tetraacetic acid, disodium salt
    0.02 g. Alkyl ($C_8$-$C_{18}$) dimethylbenzammonium chloride
    92.6 g. Water
14. 1 g. Tartaric acid
    2 g. 2,4-Dimethyl-6-Hydroxy-1,3-Dioxane
    0.5 g. Sodium dioctyl sulfosuccinate
    0.1 g. (Ethylenedinitrilo) tetraacetic acid, disodium salt
    0.1 g. 4-Chloro-3-methylphenol
    96.3 g. Water
15. 5 g. Sodium carbonate
    5 g. 2,4-Dimethyl-6-Hydroxy-1,3-Dioxane
    90 g. Water
16. 10 g. Sodium bicarbonate
    0.2 g. 2,4-Dimethyl-6-Hydroxy-1,3-Dioxane
    89.8 g. Water
17. 1 g. Potassium carbonate
    3 g. 2,4-Dimethyl-6-Hydroxy-1,3-Dioxane
    96 g. Water
18. 8 g. Disodium hydrogen phosphate
    1.5 g. 2,4-Dimethyl-6-Hydroxy-1,3-Dioxane
    90.5 g. Water
19. 3 g. Potassium carbonate
    1 g. 2,4-Dimethyl-6-Hydroxy-1,3-Dioxane
    0.02 g. Nonylphenoxypoly (2–12) ethyleneoxyethanol
    96 g. Water
20. 6.5 g. Potassium bicarbonate
    1.5 g. 2,4-Dimethyl-6-Hydroxy-1,3-Dioxane
    5 g. Benzene alkyl ($C_4$-$C_{15}$) sulfonate
    87 g. Water
21. 10 g. Sodium Carbonate
    5 g. 2,4-Dimethyl-6-Hydroxy-1,3-Dioxane
    3 g. Nonylphenoxypoly (2–12) ethyleneoxyethanol
    1 g. (Ethylenedinitrilo) tetraacetic acid, disodium salt
    81 g. Water
22. 8 g. Sodium bicarbonate
    0.2 g. 2,4-Dimethyl-6-Hydroxy-1,3-Dioxane
    2 g. Triethanolamine dodecylbenzenesulfonate
    0.1 g. (Ethylenedinitrilo) tetraacetic acid, tetrasodium salt
    89.7 g. Water
23. 10 g. Sodium bicarbonate
    1 g. 2,4-Dimethyl-6-Hydroxy-1,3-Dioxane
    0.5 g. Sodium dioctyl sulfosuccinate
    0.5 g. (Ethylenedinitrilo) tetraacetic acid, tetrasodium salt
    0.02 g. Alkyl ($C_8$-$C_{18}$) dimethylbenzammonium chloride
    88 g. Water
24. 10 g. Disodium hydrogen phosphate
    2.5 g. 2,4-Dimethyl-6-Hydroxy-1,3-Dioxane
    0.2 g. Sodium dioctyl sulfosuccinate
    0.2 g. (Ethylenedinitrilo) tetraacetic acid, disodium salt
    0.5 g. Sodium propionate
    86.6 g. Water
25. 1 g. benzoic acid
    2 g. maleic acid
    0.8 g. 2-phenyl-4-methyl-6-Hydroxy-1,3-Dioxane
    30 g. isopropanol
    66.2 g. Water
26. 5 g. glycolic acid
    1 g. 2-benzyl-4-methyl-6-Hydroxy-1,3-Dioxane
    39 g. isopropanol
    55 g. Water
27. 3 g. pyruvic acid
    2 g. crude 1,3-Dioxane reaction product of equimolar proportions of acetaldehyde, propionaldehyde and octylaldehyde
    2 g. poly(10)ethyleneoxy stearyl ether
    93 g. Water
28. 4 g. lactic acid
    0.2 g. 2,4-dimethyl-6-Hydroxy-1,3-Dioxane
    0.1 g. 2,4-dibenzyl-5-phenyl-6-Hydroxy-1,3-Dioxane
    1 g. poly(10)ethyleneoxy stearyl ether
    94.6 g. Water
29. 8 g. benzoic acid
    1 g. 2,4-dimethyl-6-Hydroxy-1,3-Dioxane
    1 g. 2,4-diethyl-5-methyl-6-Hydroxy-1,3-Dioxane
    3 g. 2,4-diheptyl-5-hexyl-6-Hydroxy-1,3-Dioxane
    3 g. sorbitan poly(20)ethyleneoxymonolaurate
    1 g. sorbitan monolaurate
    43 g. isopropanol
    40 g. Water
30. 4 g. maleic acid
    0.3 g. 2-cuminyl-4-ethyl-5-methyl-6-Hydroxy-1,3-Dioxane
    0.2 g. 2-phenyl-4-methyl-6-Hydroxy-1,3-Dioxane
    0.5 g. poly(5–10)oxyethylene fatty ($C_{11}$-$C_{15}$) ether
    44.5 g. isopropanol
    50 g. Water
31. 3 g. fumaric acid
    0.2 g. 2,4-dimethyl-6-Hydroxy-1,3-Dioxane
    1 g. 2-cuminyl-4-ethyl-5-methyl-6-Hydroxy-1,3-Dioxane
    0.5 g. 2,4-diheptyl-5-hexyl-6-Hydroxy-1,3-Dioxane
    0.1 g. octylphenoxypoly(8)ethyleneoxyethanol
    95.2 g. isopropanol
32. 1 g. maleic acid
    0.1 g. 2,4-dimethyl-6-Hydroxy-1,3-Dioxane
    0.2 g. 2,4-diethyl-5-methyl-6-Hydroxy-1,3-Dioxane
    0.5 g. nonylphenoxypoly(2–12)ethyleneoxyethanol
    98.2 g. Water
33. 6.5 g. citric acid monohydrate
    3 g. 2,4-diethyl-5-methyl-6-Hydroxy-1,3-Dioxane
    0.5 g. nonylphenoxypoly(2–12)ethyleneoxyacetamide
    60.9 g. Water
34. 10 g. glycolic acid, 70%
    0.2 g. 2,4-diheptyl-5-hexyl-6-Hydroxy-1,3-Dioxane
    0.2 g. tetrasodium ethylenedinitrilo tetraacetate
    0.5 g. nonylphenoxypoly(2–12)ethyleneoxyethanol
    30 g. isopropanol
    59.1 g. Water
35. 4.7 g. 85% lactic acid
    3.2 g. 70% glycolic acid
    0.16 g. 2,4-dibenzyl-5-phenyl-6-Hydroxy-1,3-Dioxane
    0.1 g. 2,4-dimethyl-6-Hydroxy-1,3-Dioxane
    0.1 g. 2,4-diethyl-5-methyl-6-Hydroxy-1,3-Dioxane
    0.1 g. 2,4-diheptyl-5-hexyl-6-Hydroxy-1,3-Dioxane
    0.2 g. octylphenoxypoly(8)ethyleneoxyethanol
    0.2 g. ethylenedinitrilotetraacetic acid
    20 g. isopropanol
    71.2 g. Water
36. 1 g. benzoic acid
    2 g. maleic acid
    0.8 g. 2,4-dimethyl-6-Hydroxy-1,3-Dioxane
    0.2 g. ethylenedinitrilo tetraacetic acid
    35 g. isopropanol
    60.9 g. Water
37. 3 g. diethanolamine
    0.1 g. 2,4-dimethyl-6-Hydroxy-1,3-Dioxane
    0.2 g. 2,4-diethyl-5-methyl-6-Hydroxy-1,3-

Examples-continued

Dioxane
0.02 g. sodium dioctylsulfosuccinate
96.68 g. Water
38. 5 g. diethanolamine
   0.1 g. 2,4-dimethyl-6-Hydroxy-1,3-Dioxane
   0.2 g. 2,4-diethyl-5-methyl-6-Hydroxy-1,3-Dioxane
   0.1 g. 2,4-diheptyl-5-hexyl-6-Hydroxy-1,3-Dioxane
   0.1 g. 2-phenyl-4-methyl-6-Hydroxy-1,3-Dioxane
   3 g. bis (poly(7-8)ethyleneoxy) fatty($C_{12}$-$C_{16}$) amine
   1 g. tetrasodium ethylenedinitrilo tetraacetate
   0.1 g. sodium lauryl sulfate
   90.4 g. Water
39. 10 g. triethanolamine
   2 g. 2,4-dimethyl-6-Hydroxy-1,3-Dioxane
   2 g. 2,4-diethyl-5-methyl-6-Hydroxy-1,3-Dioxane
   0.1 g. 2,4-dibenzyl-5-phenyl-6-Hydroxy-1,3-Dioxane
   0.5 g. 2-phenyl-4-methyl-6-Hydroxy-1,3-Dioxane
   41 g. isopropanol
   44.4 g. Water
40. 2.0 g. 2,4-diethyl-5-methyl-6 hydroxy-1,3-Dioxane
   2.0 g. 2,4-diheptyl-5-hexyl-6-hydroxy-1,3-Dioxane
   1.0 g. 2,4-dibenzyl-5-phenyl-6-hydroxy-1,3-Dioxane
   95 g. low volatility hydrocarbon liquid (Stoddard solvent, b.p. 310° – 375° F.)
41. .17 g. 2,4-diethyl-5-methyl-6-hydroxy-1,3-Dioxane
   25 g. propylene glycol
42. .27 g. 2-cuminyl-4-ethyl-5-methyl-6-hydroxy-1,3-Dioxane
   .19 g. 2-phenyl-4-methyl-6-hydroxy-1,3-Dioxane
   50 g. propylene glycol Hereinabove I disclose various deodorant compositions each of which includes a compound having the structure

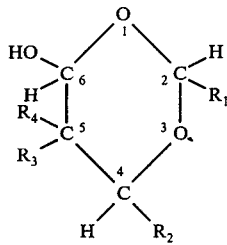

wherein $R_1$ and $R_2$ are alkyl, aryl, alkaryl or aralkyl, and $R_3$ and $R_4$ are alkyl, aryl, alkaryl, aralkyl or hydrogen, and each of which is decomposable with the liberation of aldehyde under ordinary conditions of use as a deodorant.

What is claimed is as follows:

1. A process for neutralizing offensive odors of animal origin which comprises applying to the odor-containing area, in an amount effective to neutralize the offensive odors, a 2, 4-disubstituted 6-hydroxy-1, 3-dioxane compound, in which the substituent group in each of the 2 and 4 positions is a lower alkyl or aryl group and said compound being decomposable with liberation of aldehyde under ordinary conditions of use as a deodorant.

2. The process of claim 1 in which the dioxane compound is 2,4-dimethyl-6-hydroxy-1,3-dioxane.

3. A process for neutralizing offensive odors of animal origin which comprises applying to the source of said odors, in an amount effective to neutralize the offensive odors, a deodorant composition comprising a volatile liquid vehicle having therein between 0.2–5 percent of a 2, 4-disubstituted 6-hydroxy-1, 3-dioxane compound, in which the substituent group in each of the 2 and 4 positions is a lower alkyl or aryl group and said compound being decomposable with liberation of aldehyde under ordinary conditions of use as a deodorant.

4. The process of claim 3 wherein said composition contains at least one organic carboxylic acid or inorganic acidic salt.

5. The process of claim 3 wherein said composition contains at least one inorganic basic salt or nonprimary organic amine.

6. A deodorant composition in a sealed container and comprising a 2, 4-disubstituted 6-hydroxy-1,3-dioxane compound in solution in a nonaqueous liquid vehicle, the substitution in each of the 2 and 4 positions of said dioxane compound being selected from the group consisting of lower alkyl and aryl groups, said compound being decomposable with liberation of aldehyde under ordinary conditions of use as a deodorant, wherein is included a surfactant which is stable in the composition and is present therein in the amount of about 0.02–5 percent and the concentration of said dioxane in the composition is between about 0.2–5 percent.

7. A deodorant composition in a sealed container and comprising a 2, 4-disubstituted 6-hydroxy-1,3-dioxane compound, the substitution in each of the 2 and 4 positions of said dioxane compound being selected from the class consisting of lower alkyl and aryl groups, said compound being decomposable with liberation of aldehyde under ordinary conditions of use as a deodorant, and a pH control compound selected from the class consisting of organic carboxylic acids, acidic inorganic salts, basic inorganic salts and nonprimary organic amines, in an aqueous liquid vehicle, said dioxane compound being present in the liquid vehicle to the extent of between about 0.2–5 percent and said pH control compound being present in concentration of 1–10 percent.

8. The deodorant composition of claim 7 wherein said vehicle includes a water-soluble alcohol.

9. The deodorant composition of claim 7 wherein is included a surfactant which is stable in the composition and is present in the range of about 0.02–5 percent.

10. The deodorant composition of claim 7 wherein is included an (ethylenedinitrilo)tetraacetic acid sodium salt in the amount of about 0.1–1 percent of said composition.

11. The deodorant composition of claim 7 wherein the pH control compound is a basic inorganic salt or a non-primary organic amine, said composition being mildly alkaline.

12. The deodorant composition of claim 9 wherein is included 0.1–1.0 percent of an (ethylenedinitrilo)tetraacetic acid sodium salt.

13. The deodorant composition of claim 12 wherein said dioxane component is 2,4-dimethyl-6-hydroxy-1,3-dioxane.

14. A deodorant composition in a sealed container and comprising about 0.2 to 5 percent of a decomposable 2, 4-disubstituted 6-hydroxy-1, 3-dioxane in a volatile liquid vehicle, the substitution in each of the 2 and 4 positions of said dioxane being selected from the class consisting of lower alkyl and aryl groups, said dioxane being decomposable with liberation of aldehyde under ordinary conditions of use as a deodorant and being in equilibrium with its aldehydic decomposition products, and containing 0.02–5 percent of a surfactant which is stable in the composition.

15. A deodorant composition in a sealed container and comprising a mixture of 2, 4-disubstituted 6-hydroxy-1, 3-dioxanes in a volatile liquid vehicle, the substitution in each of the 2 and 4 positions of each of said dioxanes being selected from the class consisting of lower alkyl and aryl groups, each of said dioxanes being in equilibrium with its aldehydic decomposition products, said dioxanes being present in the liquid vehicle to the extent of about 0.2–5 percent.

* * * * *